US010518052B1

(12) United States Patent
Hood

(10) Patent No.: US 10,518,052 B1
(45) Date of Patent: Dec. 31, 2019

(54) OBSTRUCTION PREVENTION DEVICE FOR ENDOTRACHEAL TUBE

(71) Applicant: Phillip Hood, Boar, AL (US)

(72) Inventor: Phillip Hood, Boar, AL (US)

(*) Notice: Subject to any disclaimer, the term of this patent is extended or adjusted under 35 U.S.C. 154(b) by 585 days.

(21) Appl. No.: 15/342,158

(22) Filed: Nov. 3, 2016

Related U.S. Application Data

(63) Continuation-in-part of application No. 14/141,909, filed on Dec. 27, 2013, now abandoned.

(51) Int. Cl.
*A61M 16/04* (2006.01)

(52) U.S. Cl.
CPC .............. *A61M 16/0497* (2013.01)

(58) Field of Classification Search
CPC ...... A61C 5/90; A61G 12/002; A61G 12/005; A61G 13/107; A61G 7/0503; A61M 16/0461; A61M 16/0463; A61M 16/0465; A61M 16/0488; A61M 16/0493; A61M 16/0495; A61M 16/0497; A61M 16/0633; A61M 16/0666; A61M 16/0672; A61M 16/0683; A61M 16/0688; A61M 16/0694; A61M 16/0816; A61M 16/0833; A61M 16/0875; A61M 2025/0206; A61M 2025/0213; A61M 2025/022; A61M 2025/0226; A61M 2025/024; A61M 2025/0246; A61M 2025/0253; A61M 2025/026; A61M 2025/0266; A61M 2202/0468; A61M 2210/0618; A61M 2210/0625; A61M 2210/0662; A61M 2230/005; A61M 25/02; A61M 5/1415; F16M 11/40; F16M 13/02;

(Continued)

(56) References Cited

U.S. PATENT DOCUMENTS

| 3,946,742 A * | 3/1976 | Eross ................ A61M 16/0488 128/207.17 |
| 4,331,143 A * | 5/1982 | Foster ............... A61M 16/0488 128/207.14 |
| 5,513,633 A | 5/1996 | Islava |

(Continued)

FOREIGN PATENT DOCUMENTS

WO 9748432 A1 12/1997

OTHER PUBLICATIONS

Universal Bite Block. Product Listing [online]. B&B Medical Technologies, 2012 [retrieved on May 9, 2013]. Retrieved from the Internet: http://bandb-medical.com/bite-proof-bite-block.

*Primary Examiner* — Annette Dixon
(74) *Attorney, Agent, or Firm* — Cramer Patent & Design, PLLC; Aaron R. Cramer

(57) ABSTRACT

A device for preventing obstruction of an endotracheal tube includes a sleeve including an open front end; an open rear end; a central cavity extending between and communicating with the front end and the rear end; and a slot extending longitudinally from the front end to the rear end to access the cavity, wherein the sleeve is configured to receive the endotracheal tube fitted within the cavity through the slot and extending through the front end and the rear end; and an anchor extending from the rear end of the sleeve, wherein the anchor includes: a top surface configured to engage the endotracheal tube; and a gripping feature disposed on the top surface configured to increase friction between the anchor and the endotracheal tube.

12 Claims, 5 Drawing Sheets

(58) Field of Classification Search
CPC ............. F16M 2200/065; Y10S 128/26; Y10S 128/911; Y10S 128/912; Y10T 24/3444; Y10T 24/44752
See application file for complete search history.

(56) References Cited

U.S. PATENT DOCUMENTS

| | | | | |
|---|---|---|---|---|
| 5,626,128 A * | 5/1997 | Bradley | ............ | A61M 16/0488 128/200.26 |
| 5,626,565 A * | 5/1997 | Landis | .................. | A61M 25/02 604/174 |
| 5,649,534 A * | 7/1997 | Briggs, III | ........ | A61M 16/0488 128/200.26 |
| 5,653,232 A * | 8/1997 | Rogers | .............. | A61M 16/0488 128/207.14 |
| 5,655,519 A | 8/1997 | Alfery | | |
| 5,803,079 A * | 9/1998 | Rogers | .............. | A61M 16/0488 128/200.26 |
| 5,934,276 A * | 8/1999 | Fabro | ................ | A61M 16/0488 128/207.14 |
| 8,096,300 B2 * | 1/2012 | Russo | ............... | A61M 16/0488 128/202.27 |
| 8,251,069 B2 | 8/2012 | Burdumy et al. | | |
| 8,256,427 B2 | 9/2012 | Chang et al. | | |
| 8,302,597 B2 | 11/2012 | Beely et al. | | |
| 2010/0180900 A1 | 7/2010 | Talsma et al. | | |
| 2014/0261462 A1 * | 9/2014 | Visconti | ............ | A61M 16/0497 128/861 |

* cited by examiner

OBSTRUCTION PREVENTION DEVICE FOR ENDOTRACHEAL TUBE

RELATED APPLICATIONS

The present invention claims the benefit of U.S. provisional application Ser. No. 61/875,295, filed Sep. 9, 2013, and is a continuation-in-part of U.S. patent application Ser. No. 14/141,909, filed Dec. 27, 2013, and the entire disclosures of which are incorporated herein by reference.

FIELD OF THE INVENTION

The present invention relates generally to medical devices and, more particularly, to a device for preventing a patient from obstructing the airway by biting an inserted endotracheal tube.

BACKGROUND OF THE INVENTION

It is often necessary to assist a patient with the breathing process while performing various medical procedures. A typical method of performing this involves intubation, which is the process of inserting an endotracheal tube into the mouth and then into the trachea, thereby providing a channel into the airway of the patient. This channel is the pathway from which a ventilator is employed to assist with breathing.

However, many times the patient becomes agitated and/or confused, resulting in the patient biting on the tube. This can prevent the ventilator from functioning properly, thus leading to inadequate respiration levels, and possible harm to the patient. Additionally, when patients bite down on the endotracheal tube, it is difficult to clear the airway of secretions that require removal.

Further, while performing other medical procedures, such as bronchoscopy, an endotracheal tube is used as a conduit through which other instruments, such as a bronchoscope, are passed through. Biting on the endotracheal tube in this situation results in costly damage to medical equipment.

Conventional endotracheal tube holders and bite blockers include mouthpieces that are inserted into a patient's mouth, through which an endotracheal tube is inserted. These apparatuses fit into a patient's mouth, filling the mouth opening, and introduce wedge-type blocks between the upper and lower rows of teeth to prop the mouth open. Many of these apparatuses necessitate the use of securement straps wrapped around a patient's head. These apparatuses add to the discomfort experienced by the patient, are cumbersome for medical workers to work with, and detract from efficacy and functionality of the rendered medical procedure. Other bite blockers include wedge-type blocks inserted into a corner of a patient's mouth and between the upper and lower rows of teeth to prop the mouth open. These do not fill the mouth opening, thereby making them more manageable; however, they have a tendency to move, and cannot be fixed in place relative to the endotracheal tube.

Accordingly, there exists a need for a means by which to prevent a patient from biting down, and closing off an endotracheal tube as well as preventing costly damage to equipment.

SUMMARY OF THE INVENTION

The inventor has recognized the aforementioned inherent problems and lack in the art and observed that there is a need for a device that prevents a patient from biting down, and closing off an endotracheal tube as well as preventing costly damage to equipment. The development of the present invention, which will be described in greater detail herein, fulfills this need.

In an embodiment, the disclosed device for preventing obstruction of an endotracheal tube includes a sleeve including an open front end, an open rear end, a central cavity extending between and communicating with the front end and the rear end, and a slot extending longitudinally from the front end to the rear end to access the cavity, wherein the sleeve is configured to receive the endotracheal tube fitted within the cavity through the slot and extending through the front end and the rear end, and an anchor extending from the rear end of the sleeve, wherein the anchor includes a top surface configured to engage the endotracheal tube, and a gripping feature disposed on the top surface configured to increase friction between the anchor and the endotracheal tube.

In an embodiment, the disclosed device for preventing obstruction of an endotracheal tube includes a sleeve including a generally elongated tubular shape having a "C"-shape in cross section, wherein the sleeve further includes an open front end, an open rear end, a base, a first curved wall extending from the base, and a second curved wall extending from the base laterally opposed to the first curved wall, wherein the first curved wall, the second curved wall, and the base define a central cavity extending between and communicating with the front end and the rear end, and wherein the first curved wall and the second curved wall converge to form the slot extending longitudinally from the front end to the rear end to access the cavity opposite the base, wherein the sleeve is configured to receive the endotracheal tube fitted within the cavity through the slot and extending through the front end and the rear end, wherein the base includes a flexible material configured to bias the first curved wall and the second curved wall in a biased position and to permit the first curved wall and the second curved wall to flex away from each other to expand the slot for insertion of the endotracheal tube, and wherein the first curved wall and the second curved wall include an inflexible material configured to resist compression of the sleeve in response to a bite of a human, an anchor extending from the rear end of the sleeve and configured to be connected to the endotracheal tube, wherein the anchor includes a top surface configured to engage the endotracheal tube; a gripping feature disposed on the top surface configured to increase friction between the anchor and the endotracheal tube, and a fastener retaining aperture disposed laterally through the anchor, wherein the gripping feature includes one (1) of an array of conical protrusions extending upwardly from the top surface of the anchor and an array of lateral teeth parallel to each other and extending upwardly from the top surface of the anchor, a hinging feature disposed between a joining interface of the sleeve and the anchor, wherein the hinging feature is configured to permit the anchor to pivot upwardly and downwardly relative to the sleeve, wherein the hinging feature is configured to bias the anchor in a biased position approximately parallel with the sleeve, wherein the hinging feature includes one (1) of a triangular notch formed in the top surface of the anchor and a semicircular notch formed in the top surface of the anchor, and a fastener configured to attach the anchor to the endotracheal tube, wherein the fastener includes a strap retainer extending through the fastener retaining aperture of the anchor and is configured to be fastened around the endotracheal tube.

In yet an embodiment, the disclosed device for preventing obstruction of an endotracheal tube includes a sleeve including an open first end, an opposing open rear end, and a slot extending longitudinally along the sleeve on a first side, wherein the sleeve has a generally elongated tubular shape, the sleeve is a translucent, plastic material, and the sleeve includes a resilient material configured to enable reception and retention of the endotracheal tube via an interference fit through the slot resist modification of the endotracheal tube due to a bite of a human, an anchor extending from a perimeter edge of the front end, wherein the anchor includes a generally rectangular shape, the anchor further includes a gripping feature including of plurality of conical protrusions extending from a top surface of the anchor, the anchor is attached to the sleeve by a hinging feature at a second side opposite the first side, the hinging feature is configured to pivot away from the first side to provide added clearance to manipulate the device while inserting the endotracheal tube within the sleeve, the hinging feature is configured to bias the anchor toward the first side, the anchor is plastic and integral to the sleeve, and the hinging feature includes a notch formed in the top surface of the anchor proximate to a location where the anchor meets the sleeve, a fastener routed through an aperture disposed through the anchor and configured to secure the device to the endotracheal tube, wherein the slot enables the sleeve to receive the endotracheal tube such that the endotracheal tube is seated within the sleeve and protrudes through the front end and second end, wherein the anchor is configured to assist with securement of the device to the endotracheal tube by abutting the gripping feature with the endotracheal tube, and wherein the fastener is configured to wrap around the endotracheal tube and fasten to secure the endotracheal tube and the device in a position relative to each other.

Furthermore, the described features and advantages of the disclosure may be combined in various manners and embodiments as one skilled in the relevant art will recognize. The disclosure can be practiced without one (1) or more of the features and advantages described in a particular embodiment.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

Figure 1:
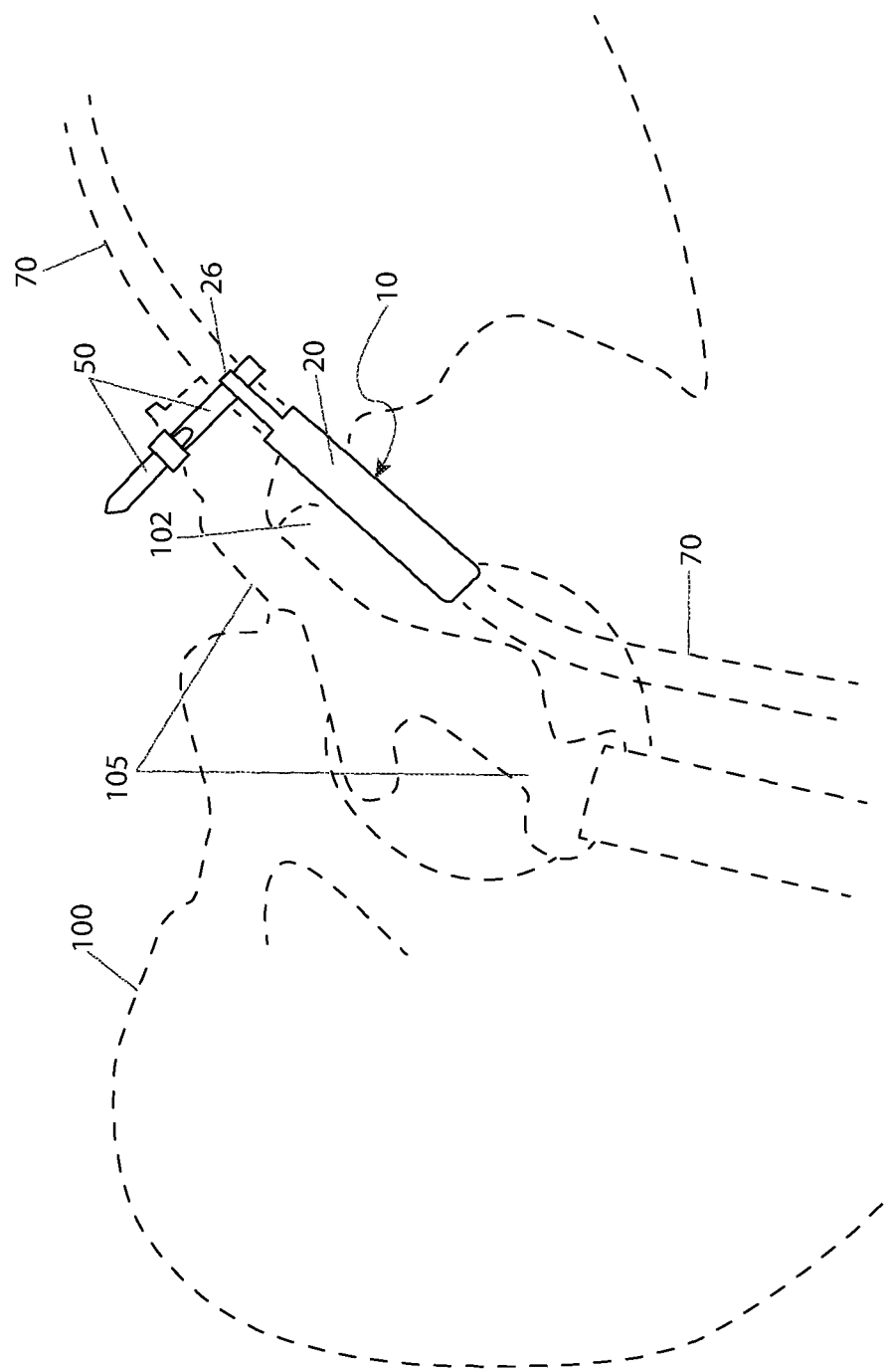
FIG. 1 is an environmental side view of an embodiment of the disclosed obstruction prevention device for an endotracheal tube.

DESCRIPTIVE KEY 10 obstruction prevention device
20 sleeve
22 slot
24*a* front opening
24*b* rear opening
26 anchor
28 hinging feature
30 fastener retaining aperture
32 gripping feature
34 body
36 cavity
38 front end
40 rear end
42 base
44 first curved wall
46 second curved wall
48 bottom surface
50 fastener
51 strap retainer
52 retainer
53 locking tab
54 upper end of first curved wall
55 strap
56 upper end of second curved wall
58 tape
60 strip
62 top surface of anchor
63 bottom surface of anchor
64 notch
66 adhesive tape
68 array of conical protrusions
70 conical protrusion
72 array of teeth
74 a plurality of teeth
100 patient
101 endotracheal tube
102 mouth
105 tube positioning apparatus

DETAILED DESCRIPTION OF THE PREFERRED EMBODIMENT

In accordance with the invention, the best mode is presented in terms of example embodiments, herein depicted within FIGS. 1-6. However, the disclosure is not limited to a single described embodiment and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only one (1) particular configuration may be shown and described for purposes of clarity and disclosure and not by way of limitation of scope.

The terms "a" and "an" herein do not denote a limitation of quantity, but rather denote the presence of at least one (1) of the referenced items.

Referring to FIGS. 1-6, disclosing an obstruction prevention device for an endotracheal tube, generally referred to herein as the "device" 10, where like reference numerals represent similar or like parts.

FIG. 1 is a schematic illustration of an environmental view of an embodiment of the disclosed device 10. The device 10 is designed and intended to prevent a patient 100 from biting an endotracheal tube 101, or similar medical apparatus, which is inserted into a mouth 102 of the patient 100. Additionally, the device 10 prevents damage to other similarly installed equipment such as bronchoscopes (not shown), which are inserted through the endotracheal tube 101 for therapeutic and diagnostic procedures.

Figure 4:
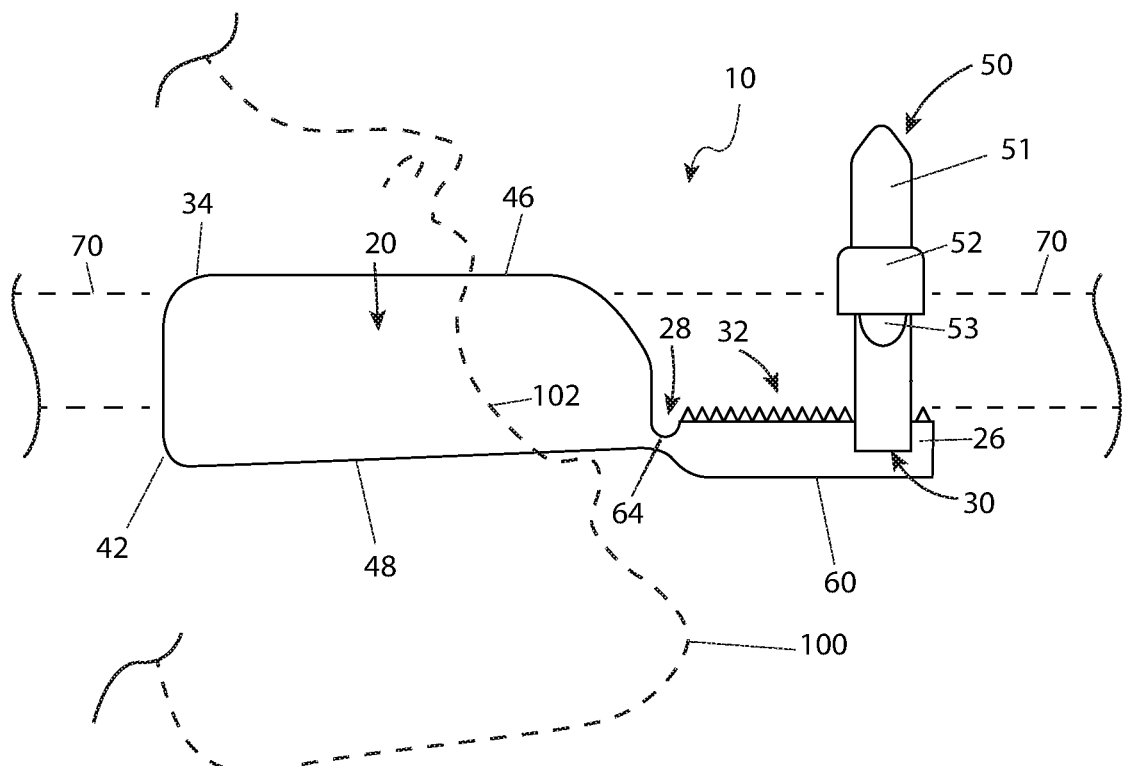
FIG. 4 is an environmental side view of another embodiment of the disclosed obstruction prevention device for an endotracheal tube.
Figure 5:
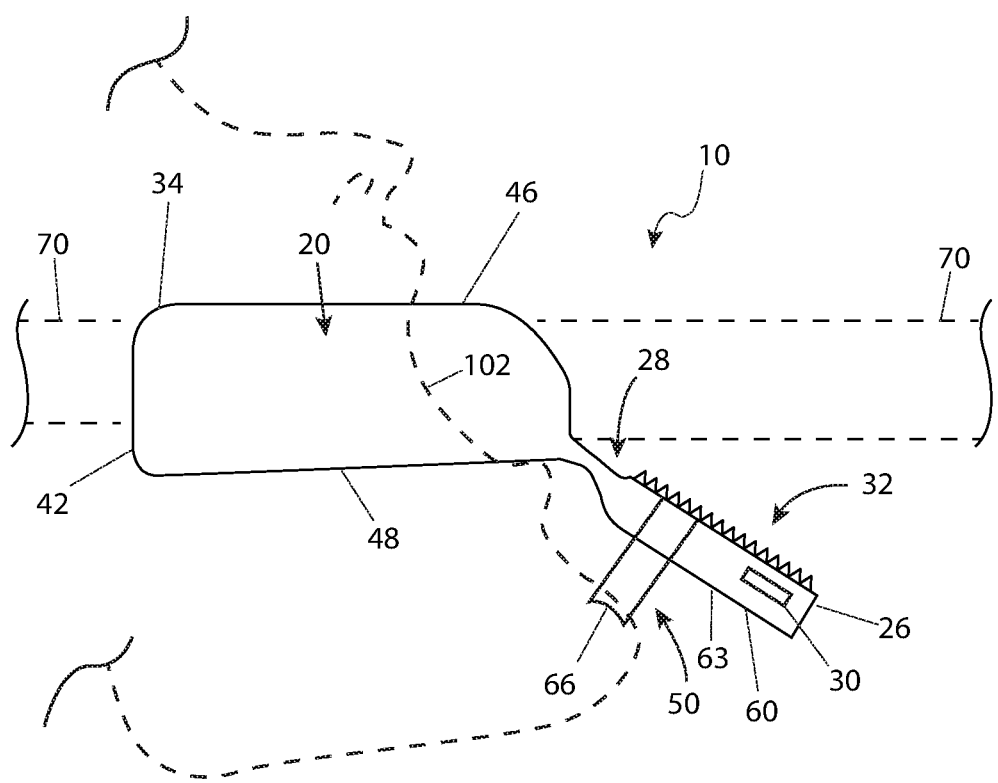
FIG. 5 is an environmental side view of another embodiment of the disclosed obstruction prevention device for an endotracheal tube; and, FIG. 6 is a top perspective view of another embodiment of the disclosed obstruction prevention device for an endotracheal tube.

As illustrated in FIG. 1, the device 10 is configured to provide accurate and stable positioning of the endotracheal tube 101 within the patient's mouth 102 and between the patient's teeth (not shown). The device 10 provides a tool to help prevent the biting of an artificial airway by the patient 100, for example, when in an intensive care unit (ICU), emergency room, or during field rescue situations. The device 10 is configured to work in conjunction or cooperation with various tube positioning apparatuses 105, for example and without limitation, an Anchor Fast™ oral endotracheal tube fastener available from Hollister Inc. of Libertyville, Ill. As an example, the device 10 may be connected to the tube positioning apparatus 105 with a provided fastener 50, as illustrated in FIGS. 1 and 4. Alternatively, the device 10 may be secured to the patient 100, for example, using medical tape and other means, as illustrated in FIG. 5.

Figure 2:
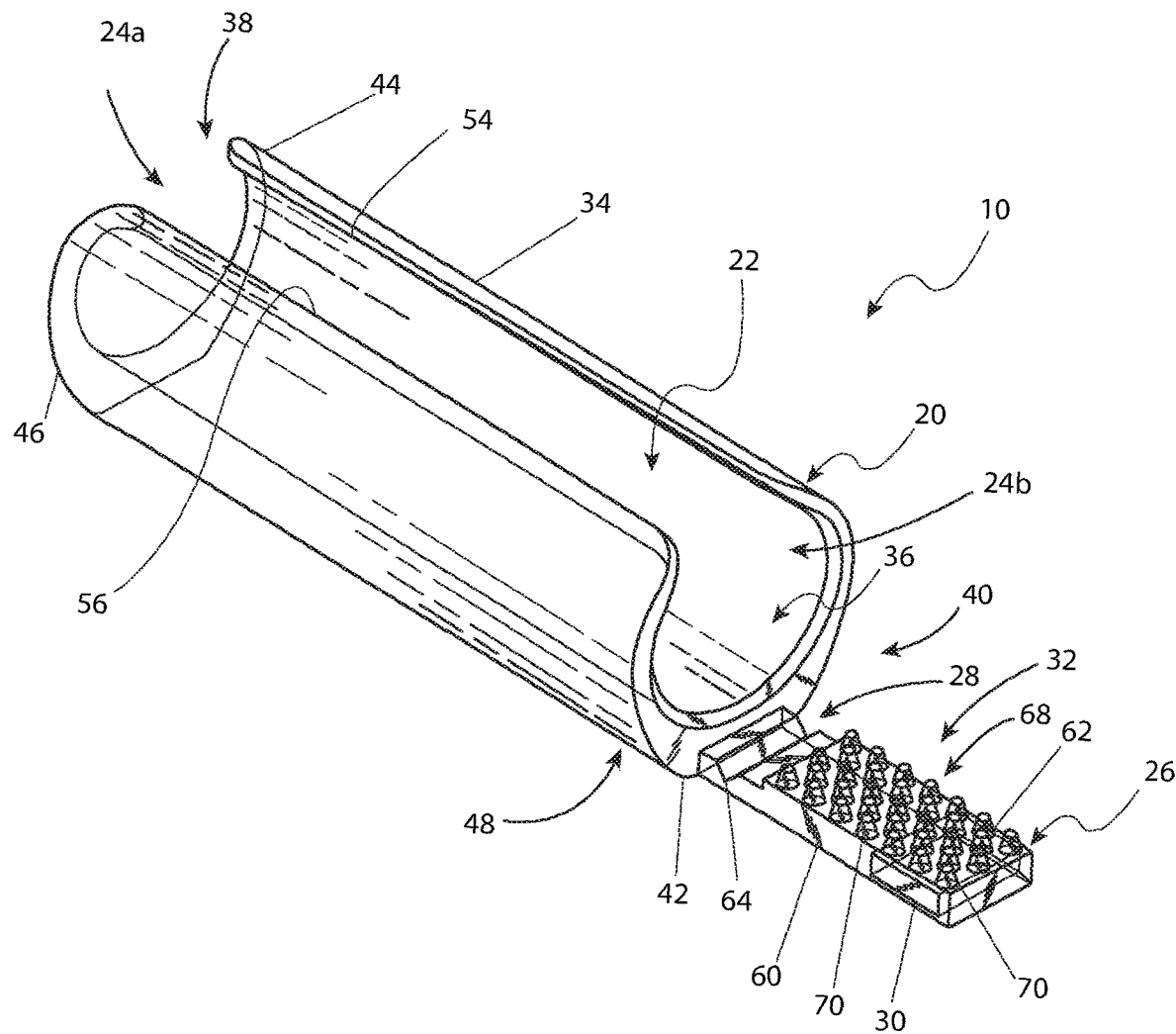
FIG. 2 is a side and top perspective view of another embodiment of the disclosed obstruction prevention device for an endotracheal tube.

FIG. 2 is a schematic illustration of a perspective view of an embodiment of the disclosed device 10. The device 10 includes a sleeve 20 and an anchor 26. The sleeve 20 includes a generally hollow cylindrical, or tubular, body 34. The body 34 includes a front end 38 and a longitudinally opposed rear end 40. The body 34 defines central cavity 36 extending from the front end 38 to the rear end 40 defining a front opening 24A (e.g., open front end) and an opposing rear opening 24B (e.g., open rear end). The endotracheal tube 101 (FIG. 1) can be slip fitted within the cavity 36 and extend from the front opening 24A and the rear opening 24B. The body 34 also includes a slot 22 extending from the front end 38 to the rear end 40 to provide access to the cavity 36 for the endotracheal tube 101. Thus, the body 34 of the sleeve 20 has an approximately "C"-shape in cross-section.

As an example, the body 34 includes a base 42. The base 42 may include a substantially flat bottom surface 48. A first curved wall 44 extends from the base 42. A second curved wall 46, laterally opposed to the first curved wall 44, extends from the base 42. Upper ends, or edges, 54, 56 of the first curved wall 44 and the second curved wall 46, respectively, converge and are spaced apart to define the slot 22 opposite the base 42.

The device 10 may have various dimensions based upon the intended use and the type of endotracheal tube 101 and/or tube positioning apparatus 105 being used. As a non-limiting example, the sleeve 20 may be approximately two and one-half inches (2½ in.) in length.

The sleeve 20 (e.g., the body 34) may define a biased inside diameter. The biased inside diameter of the body 34 in the biased or unflexed position may be slightly smaller, for example, less than five percent (5%) smaller, that the outside diameter of the endotracheal tube 101 being used, such that the body 34 (e.g., the first curved wall 44 and the second curved wall 46) resiliently and forcefully grips around the endotracheal tube 101 disposed within the cavity 36. As a non-limiting example, the biased inside diameter of the sleeve 20 (e.g., the body 34) may be approximately one-half inch (2 in.). However, in other examples, the device 10 may be suitably sized to receive and retain a range of endotracheal tubes 70 ranging from size six (6) to size nine (9).

When the body 34 is in the biased or unflexed position, the linear dimension of the slot 22 (e.g., the distance between the ends 54, 56) may be less than the outside diameter of the endotracheal tube 101. As a non-limiting example, when the body 34 is in the biased position, the slot 22 may be approximately one-quarter of an inch (¼ in.) wide. When the body 34 is in the unbiased or flexed position, the linear dimension of the slot 22 (e.g., the distance between the ends 54, 56) may be increased to be greater than the outside diameter of the endotracheal tube 101, which allows the device 10 to be clipped onto the endotracheal tube 101.

Figure 3:
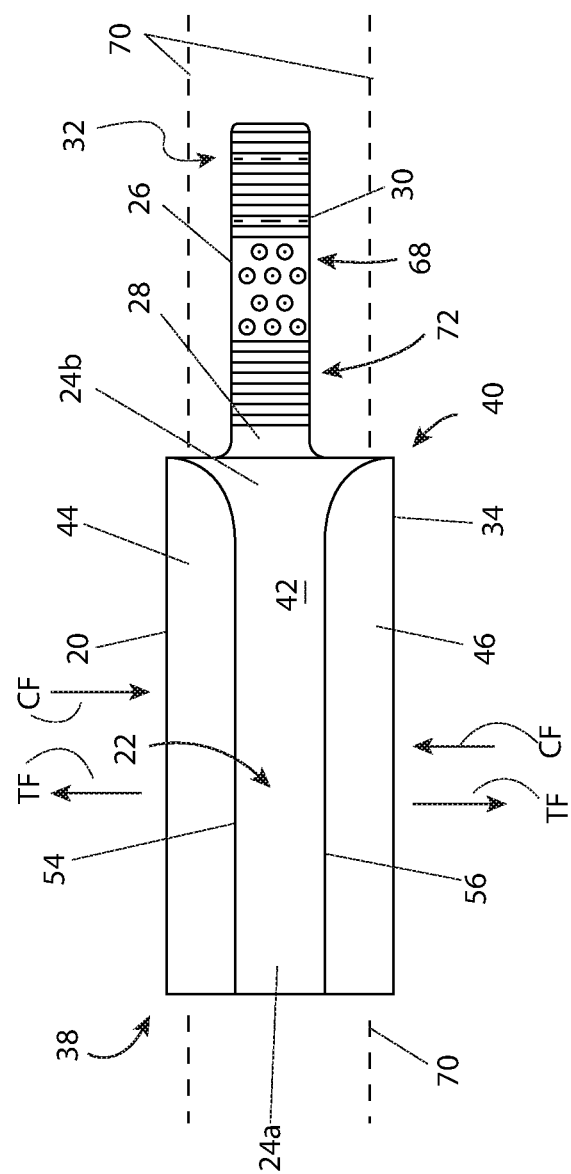
FIG. 3 is top view of another embodiment of the disclosed obstruction prevention device for an endotracheal tube.

FIG. 3 is a schematic illustration of a top view of an embodiment of the device 10, illustrated with the endotracheal tube 101 fitted within the body 34. In an example embodiment, the base 42 may be made of a flexible resilient material configured to bias the first curved wall 44 and the second curved wall 46 into the biased position, thereby defining the biased or unflexed inside diameter of the body 34. In the biased position, the body 34 (e.g., the first curved wall 44 and the second curved wall 46) exerts a compression force CF on the endotracheal tube 101 acting in a plane approximately parallel with a plane of the slot 22. The base 42 may also be configured to permit the first curved wall 44 and the second curved wall 46 to be separated, for example, by moving the respective upper ends 54, 56 apart in response to a tension force TF acting in a plane approximately parallel to the plane of the slot 22, thereby temporarily increasing the size of the slot 22 and the inside diameter of the body 34 for insertion of the endotracheal tube 101. The first curved wall 44 and the second curved wall 46 may be made of an inflexible material that is resistant to pinching or crushing due to being bitten down on by the patient's teeth, for example, in response to a compression force acting in a plane approximately perpendicular to the plane of the slot 22. In other words, the sleeve 20 may be flexible enough to allow the endotracheal tube 101 to be fitted within the cavity 36, yet be rigid enough to not allow biting down on the sleeve 20 to modify the shape of the endotracheal tube 101.

In an example embodiment, the sleeve 20 (e.g., the body 34 including the gripping feature 32 and first and second curved walls 44, 46) may be made of a plastic material. As an example, the sleeve 20 may be preferably made of a transparent (e.g., completely clear) plastic material to allow a medical worker the ability to see any indicia (e.g., numbers or other markings) that may appear upon the endotracheal tube 101 providing an aid for proper insertion. As another example, the sleeve 20 may be preferably made of a translucent (e.g., partially clear or semitransparent) plastic material to allow a medical worker the ability to see any indicia (e.g., numbers or other markings) that may appear upon the endotracheal tube 101 providing an aid for proper insertion.

Referring to FIGS. 2 and 3, the anchor 26 is connected to and extends from the rear end 40 of the body 34. As an example, the anchor 26 is connected to and extends longitudinally from the base 42. In an example embodiment, the sleeve 20 and the anchor 26 may be integrally molded to form a unitary molded structure. The anchor 26 includes a thin strip 60 of material. In an example embodiment, the anchor 26 (e.g., the strip 60) may be made of a narrow, elongated (e.g., rectangular) piece of a plastic material. The anchor 26 also includes a gripping feature 32 disposed on a top surface 62 of the strip 60.

The anchor 26 is configured to be biased into a position parallel with the base 42. However, the anchor 26 is also configured to flex downwardly, for example, in response to a downward force applied to the strip 60 or upwardly, for example, in response to an upward force applied to the strip 60. In an example embodiment, the anchor 26 includes a hinging feature 28. The hinging feature 28 is configured to permit downward flexing of the anchor 26 relative to the sleeve 20. As illustrated in FIG. 2, as an example, the hinging feature 28 includes a notch 64 formed in the top surface 62 of the strip 60 and extending downwardly into the strip 60. As an example, the notch 64 may have a triangular shape, as illustrated in FIG. 2. As another example, the notch 64 may have a semicircular shape, as illustrated in FIG. 4. The notch 64 may be located proximate to a joining interface between the anchor 26 and the sleeve 20. Alternatively, as another example, the hinging feature 28 is formed by a reduction in the thickness of the strip 60 proximate to the sleeve 20.

FIG. 4 is a schematic illustration of an environmental side view of an embodiment of the disclosed device, illustrating a first manner of securing the device 10. As illustrated in FIG. 4, in an embodiment, the anchor 26 is configured to securely attach the device 10 to the endotracheal tube 101. The anchor 26 may be attached to the endotracheal tube 101, for example, using the fastener 50. As an example, the fastener 50 may be a strap retainer 51, also referred to as a tie-wrap or cable tie. The strap retainer 51 may connect the anchor 26 to an appropriate position upon the endotracheal tube 101 in order to appropriately position the sleeve 20 relative to the endotracheal tube 101 and the patient's mouth 102. If needed, the anchor 26 may pivot upwardly, about the hinging feature 28, relative to the sleeve 20 in order for the top surface 62 of the strip 60 to make contact with and engage the endotracheal tube 101.

Figure 6:
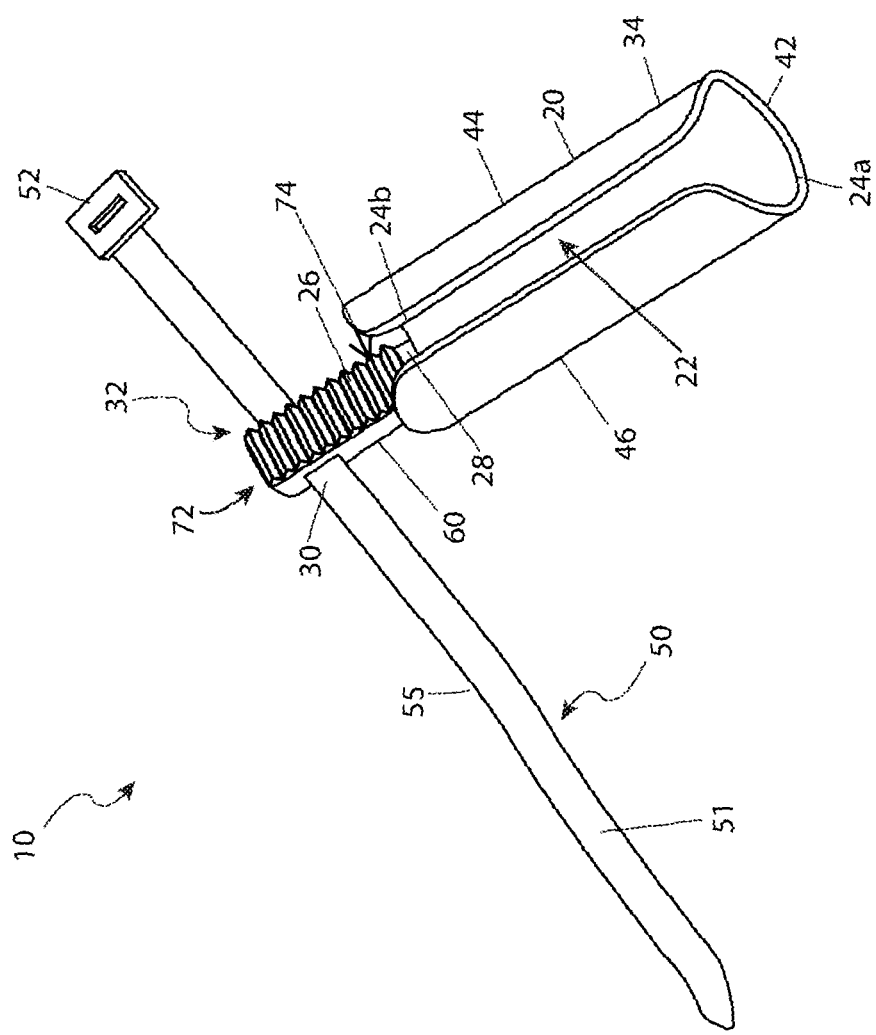

FIG. 6 is a schematic illustration of a top perspective view of the device 10, illustrated with the strap retainer 51 connected to the anchor 26. In an embodiment, and as also illustrated in FIGS. 1, 2 and 4, the anchor 26 may be configured to receive and retain the fastener 50. In an embodiment, the anchor 26 includes a fastener retaining aperture 30 formed (e.g., integrally-molded) within or otherwise disposed through the strip 60. As an example, the fastener retaining aperture 30 may be located at or near a free end of the anchor 26 opposite the sleeve 20, thereby enabling correct positioning of the sleeve 20 with respect to the patient's mouth 102. In the illustrative embodiment, the fastener retaining aperture 30 includes a rectangular opening extending laterally through the strip 60 of the anchor 26. The fastener retaining aperture 30 is suitably sized to receive (e.g., by sliding insertion of) the fastener 50. As an example, the fastener retaining aperture 30 is sized to receive the strap retainer 51, as illustrated in FIG. 6.

Alternatively, the strap retainer 51 may be wrapped around the anchor 26 and the endotracheal tube 101, for example, without extending through the fastener retaining aperture 30.

The strap retainer 51 is configured to stabilize and position the device 10 upon the endotracheal tube 101, for example, by passing a strap 55, or tail, through the fastener retaining aperture 30, wrapping the strap 55 around the endotracheal tube 101, and tightening the strap retainer 51 by engaging the strap 55 with an integral retainer 52 of the strap retainer 51 in a conventional manner. In an example embodiment, the strap retainer 51 may be of a re-usable style, for example, having a locking tab 53 (FIG. 4) or similar mechanism to release tension upon the strap 55, allowing a user to reposition the endotracheal tube 101, and re-tighten the strap retainer 51 upon the endotracheal tube 101. The strap retainer 51 may be any of various commercially-available strap retainers, for example and without limitation, as sold by YUEQUIG YUTAI PLASTIC MANUFACTURING CO.®, CABLEORGANIZER.COM, INC.®, and others.

In an example implementation, the device 10 may be utilized as a single-use device and packaged with one (1) strap retainer 51.

FIG. 5 is a schematic illustration of an environmental side view of an embodiment of the disclosed device, a second manner of securing the device 10. As illustrated in FIG. 5, in an embodiment, the anchor 26 is configured to securely attach the device 10 to the patient's mouth 102. The anchor 26 may be attached to the patient 100, for example, using the fastener 50. As an example, the fastener 50 may be a strip of adhesive tape 66. The adhesive tape 66 may be placed over top of the anchor 26 and adhered to an appropriate location on the patient's face (e.g., on the chin) in order to appropriately position the sleeve 20 relative to the endotracheal tube 101 and the patient's mouth 102. If needed, the anchor 26 may pivot downwardly, about the hinging feature 28, relative to the sleeve 20 in order for a bottom surface 63 of the strip 60 to make contact with and engage the patient's skin.

Alternatively, the strip of adhesive tape 66 may extend through the fastener retaining aperture 30.

Referring to FIGS. 2-6, in an embodiment, the top surface 62 of the strip 60 of the anchor 26 includes a gripping feature 32. The gripping feature 32 is configured to increase friction between the engaged top surface 62 and the endotracheal tube 101, for example, to prevent linear movement of the device 10 relative to the endotracheal tube 101 before and/or after installation of the strap retainer 51. In an example embodiment, the gripping feature 32 may be integrally molded with the strip 60 of the anchor 26.

Referring to FIG. 2, in an embodiment, the gripping feature 32 includes an array of conical protrusions 68 extending upwardly from the top surface 62 of the strip 60 of the anchor 26. As an example, each conical protrusion 70 may be truncated, that is, each conical protrusion 70 may be a truncated cone having a flat top surface. As another example, each conical protrusion 70 may a cone having a pointed apex. The array of conical protrusions 68 may have any configuration, layout or pattern. As an example, the conical protrusions 70 may be aligned longitudinally and/or laterally upon the top surface 62 of the strip 60. As another example, alternating rows and/or columns of conical protrusions 70 may be offset relative to each other.

Referring to FIG. 6, in an embodiment, the gripping feature 32 includes an array of teeth 72 of a plurality of teeth 74 extending upwardly from the top surface 62 of the strip 60 of the anchor 26. As an example, each tooth 74 may be formed by alternating parallel triangular ridges and grooves formed in the top surface 62. The teeth 74 may be parallel to each other and extend laterally across the top surface 62.

Referring to FIG. 3, in an embodiment, the gripping feature 32 includes a combination of the array of conical protrusions 68 and the array of teeth 72.

In another embodiment (not shown), the gripping feature 32 may include knurling formed on the top surface 62 of the strip 60 of the anchor 26. As an example, a pattern of straight, angled or crossed lines may be cut or rolled into the the top surface 62.

It is envisioned that other styles and configurations of the disclosed device 10 can be easily incorporated into the teachings of the present disclosure, and only particular example embodiments have been shown and described for purposes of clarity and disclosure and not by way of limitation of scope.

The various disclosed embodiments of the device 10 can be utilized by the user in a simple and straightforward manner with little or no training. As an example, the device 10 may be configured and utilized as indicated in FIGS. 1, 4 and 5.

An example embodiment of the disclosed method of installing and utilizing the device 10 may be achieved by performing the following steps: 1). procuring a model of the device 10 having an inside diameter that corresponds to a particular endotracheal tube 101 being used; 2). assessing a proper placement position for the device 10 upon the endotracheal tube 101; 3). optionally, installing any additional desired tube positioning apparatus 105; 4). inserting the endotracheal tube 101 through the slot 22 of the sleeve 20; 5). positioning the device 10 at a desired position along the endotracheal tube 101; 6). pivoting the anchor 26 about the hinging feature 28 toward either the endotracheal tube 101 or the mouth 102 of the patient 100; 7). engaging the anchor 26 against either the endotracheal tube 101 or the patient 100; 8). securing the anchor 26 to either the endotracheal tube 101 or the patient 100, for example, by utilizing the fastener 50; 9). utilizing the endotracheal tube 101 to deliver gases, anesthetic agents, administer medications, perform airway management, perform critical care, deliver instrumentation, perform mechanical ventilation, and the like; and, benefiting from a versatile and secure positioning of an endotracheal tube 101 within a patient's mouth 102 afforded a user of the device 10.

The relative position of the device 10 upon the endotracheal tube 101 may be adjusted as needed, for example, by performing the following steps: 1). releasing the fastener 50; 2). angling the anchor 26 away from either the endotracheal tube 101 or the patient 100; 3). adjusting the relative position of the device 10 and endotracheal tube 101 as desired; 4). pivoting the anchor 26 about the hinging feature 28 toward either the endotracheal tube 101 or the mouth 102 of the patient 100; 5). re-engaging the anchor 26 against either the endotracheal tube 101 or the patient 100; and 6). re-securing the anchor 26 to either the endotracheal tube 101 or the patient 100, for example, by utilizing the fastener 50.

Thus, the disclosed device 10 offers various advantages including enabling prevention of a patient 100 from biting down onto the endotracheal tube 101 and hold the endotracheal tube 101 in place by being slid onto the endotracheal tube 101. Further, the device 10 enables a single solution to be used with various sized endotracheal tubes 101. Further, the device 10 enables securement to the endotracheal tube 101 as well as to any ancillary tube positioning apparatus 105. Further, the device 10 enables holding the endotracheal tube 101 in place in a patient's mouth 102 by way of a strap retainer 51 or adhesive tape 66, if an ancillary tube positioning apparatus 105 is unavailable. Further, the device 10 does not fill the entire mouth opening 102 of the patient 100 while in use. Further, the device 10 enables securement in a fixed position relative to the endotracheal tube 101, but also be repeatedly adjusted in relative position. Further, the device 10 enables augmented securement of the fixed-relative position by way of the gripping feature 32. An added benefit of the device 10 is to provide a device that is translucent so as to not frustrate the ability to read any indicia displayed on the endotracheal tube 101.

The foregoing descriptions of specific embodiments have been presented for purposes of illustration and description. They are not intended to be exhaustive or to limit to the precise forms disclosed and many modifications and variations are possible in light of the above teachings. The embodiments were chosen and described in order to best explain principles and practical application to enable others skilled in the art to best utilize the various embodiments with various modifications as are suited to the particular use contemplated.

The invention claimed is:

1. A device for preventing obstruction of an endotracheal tube, comprising:
 a sleeve, comprising:
  an open front end;
  an open rear end;
  a central cavity extending between and communicating with said front end and said rear end; and
  a slot extending longitudinally from said front end to said rear end to access said cavity;
  wherein said sleeve is configured to receive said endotracheal tube fitted within said cavity through said slot and extending through said front end and said rear end; and
 an anchor extending from said rear end of said sleeve, wherein said anchor comprises:
  a top surface configured to engage said endotracheal tube; and
  a gripping feature disposed on said top surface configured to increase friction between said anchor and said endotracheal tube;
 wherein said sleeve comprises a plastic material, and wherein said plastic material is one of transparent and translucent;
 further comprising a hinging feature disposed between a joining interface of said sleeve and said anchor, wherein said hinging feature permits said anchor to pivot upwardly and downwardly relative to said sleeve;
 wherein said hinging feature is biased to said anchor in a biased position parallel with said sleeve;
 wherein said hinging feature comprises a triangular notch formed in said top surface of said anchor.

2. The device of claim 1, wherein said sleeve is configured to resist compression of said endotracheal tube fitted within said cavity in response to a bite of a human.

3. The device of claim 1, wherein said sleeve comprises a generally elongated tubular shape having a C-shape in cross section.

4. The device of claim 1, wherein said sleeve further comprises:
 a base;
 a first curved wall extending from said base; and
 a second curved wall extending from said base laterally opposed to said first curved wall;
 wherein said first curved wall and said second curved wall converge to form said slot opposite said base.

5. The device of claim 4, wherein said base comprises a flexible material configured to bias said first curved wall and said second curved wall in a biased position and to permit said first curved wall and said second curved wall to flex away from each other to expand said slot for insertion of said endotracheal tube, and,
 wherein said first curved wall and said second curved wall comprise an inflexible material configured to resist compression of said sleeve in response to a bite of a human.

6. The device of claim 5, wherein said sleeve comprises a biased inside diameter that is less than five percent smaller than an outside diameter of said endotracheal tube and configured to retain said endotracheal tube by circumferential compression.

7. The device of claim 1, wherein said anchor comprises a generally rectangular shape.

8. The device of claim 1, wherein said gripping feature comprises an array of conical protrusions extending upwardly from said top surface of said anchor.

9. The device of claim 1, wherein said gripping feature comprises an array of lateral teeth parallel to each other and extending upwardly from said top surface of said anchor.

10. The device of claim 1, wherein said anchor is configured to be connected to said endotracheal tube, wherein said device further comprises a fastener configured to attach said anchor to said endotracheal tube, and wherein said anchor further comprises a fastener retaining aperture configured to receive said fastener.

11. The device of claim 10, wherein said fastener comprises a strap retainer.

12. The device of claim 1, wherein said anchor is configured to be connected to said a patient, wherein said device further comprises a fastener configured to attach said anchor to said patient, and wherein said fastener comprises a strip of adhesive tape.

\* \* \* \* \*